(12) United States Patent
Besse et al.

(10) Patent No.: US 7,033,606 B1
(45) Date of Patent: Apr. 25, 2006

(54) PHARMACEUTICAL COMPOSITION INTENDED IN PARTICULAR FOR THE PREVENTION AND THE TREATMENT OF RADIOMUCOSITIS AND CHEMOMUCOSITIS

(75) Inventors: Jérôme Besse, Pessac (FR); Tam Nguyen, Maisons-Alfort (FR); Joëlle Leyder, Maisons-Alfort (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/764,990

(22) PCT Filed: Jul. 19, 1999

(86) PCT No.: PCT/FR99/01760

§ 371 (c)(1),
(2), (4) Date: Jan. 22, 2001

(87) PCT Pub. No.: WO00/04878

PCT Pub. Date: Feb. 3, 2000

(30) Foreign Application Priority Data

Jul. 20, 1998 (FR) ................... 98 09230

(51) Int. Cl.
*A61F 13/02* (2006.01)
*A61K 9/14* (2006.01)

(52) U.S. Cl. ............. 424/435; 424/434; 424/484; 424/485; 424/486; 424/488

(58) Field of Classification Search ............ 424/434, 424/404, 725, 484, 485, 486, 488, 435
See application file for complete search history.

(56) References Cited

U.S. PATENT DOCUMENTS

| 4,748,022 A | * | 5/1988 | Busciglio ............ 424/195.1 |
| 5,281,196 A | | 1/1994 | Sultenfuss ............. 604/20 |
| 5,858,371 A | | 1/1999 | Singh et al. ........... 424/195.1 |
| 5,952,373 A | * | 9/1999 | Lanzendorfer et al. ..... 514/456 |
| 6,316,012 B1 | * | 11/2001 | N'Guyen et al. .......... 424/401 |
| 6,333,044 B1 | * | 12/2001 | Santus et al. ............ 424/434 |

FOREIGN PATENT DOCUMENTS

| EP | 0 380 368 A1 | 8/1990 |
| EP | 0 386 960 A2 | 9/1990 |
| EP | 0 577 143 A2 | 1/1994 |
| EP | 0 648 496 A1 | 4/1995 |
| WO | WO 93/21905 | 11/1993 |

OTHER PUBLICATIONS

Kostler et al, Oral Mucositis Complicating Chemotherapy and/or Radiotherapy. Options for Prevtnion and Treatment, CA Cancer J Clin 2001; 51:290-315.*

* cited by examiner

*Primary Examiner*—Carlos A. Azpuru
(74) *Attorney, Agent, or Firm*—Woodcock Washburn LLP

(57) ABSTRACT

The invention concerns a pharmaceutical composition designed to adhere to a mucous membrane for preventing or treating radiotherapy-related and chemotherapy-related mucositis, induced by radiotherapy or combined radio-chemotherapy, comprising an effective amount of an anti-radical compound mixed with a vehicle, which is liquid at room temperature and gels at the mucous membrane temperature and capable of adhering to the mucous membrane by its gelled status.

24 Claims, No Drawings

PHARMACEUTICAL COMPOSITION INTENDED IN PARTICULAR FOR THE PREVENTION AND THE TREATMENT OF RADIOMUCOSITIS AND CHEMOMUCOSITIS

CROSS REFERENCE TO RELATED APPLICATIONS

This application represents entry into the United States under 35 U.S.C. § 371 of International Application PCT/FR99/01760, filed Jul. 19, 1999, which in turn claims priority of the French national application serial no. France 98 09 230, filed Jul. 20, 1998.

The present invention relates to a pharmaceutical composition intended in particular for the prevention and the treatment of radiomucositis and of mucositis induced by anticancer polychemotherapies.

From the data collected during the period 1987–1992 among its member countries, the World Health Organization (WHO) calculated (for the year 1994) an estimation of the incidence of cancers, according to gender, on a global scale (World Health Organization: World Health Statistics Annuals, 1987–1992—Geneva, Switzerland, WHO): in men, the location characterized by the highest incidence is the prostate (32%); in women, the highest incidence is breast cancer (32%). In men, cancers of the head and neck as well as of the oropharyngeal cavity have an incidence of close to 6% and the incidence of colorectal cancers is 12%. In women, the incidence of cancers of the "head and neck, and the oropharyngeal cavity" is 5% and that of colorectal cancer 13% while the incidence of uterine cancers is 8%. These figures speak for themselves and show immediately the extent of the problem posed by the taking into account of the side effects of antimitotic treatments used, in particular antiproliferative polychemotherapies and radiotherapy.

Depending on their location, cancer therapy frequently involves medium- or high-energy radiotherapy either as a first line treatment, or as an adjuvant therapy to surgery and chemotherapy. Radiotherapy is in particular widely used for the treatment of certain locations: head and neck; brain; oropharyngeal cavity; oesophagus and stomach; large intestine and rectum; uterus. In 1994, the incidence of new cases of cancer in these locations was estimated by the National Cancer Institute (NCI), for the population of the United States:

| | |
|---|---|
| head and neck, brain: | 17,500 new cases |
| oropharyngeal cavity: | 29,600 new cases |
| larynx: | 12,500 new cases |
| oesophagus and stomach: | 35,000 new cases |
| colon and rectum: | 150,000 new cases |
| uterus: | 46,000 new cases. |

By virtue of the advances in computerized axial tomography, the determination of irradiation fields, the kinetics of irradiation as well as the rates of radiation doses have been improved regularly. Accordingly, for "head and neck" cancers, it is now known that the period between surgical exeresis and radiotherapy should not exceed 6 weeks and that any interruption in the radiotherapy—even in the event of severe adverse effects—is prejudicial to its efficacy. Even more, it is known that certain tumours require an acceleration of the radiotherapy (dose intensification) in order to reach more effectively a larger number of tumour cells when these are in the dividing phase: this is hyperfractionated radiotherapy. In the same spirit, the constant search for potentiation of the therapeutic effect has led to the evaluation of alternate radiochemotherapy and to protontherapy which allows the irradiation to be very finely focused.

Radiotherapy-based irradiation of a cancer of the oesophagus or of the larynx leads to the appearance of a painful dysphagia, a source of an intense functional discomfort (which can cause substantial loss of weight), by attack on the mucous membrane by the ionizing radiation. Likewise, the irradiation of abdominal adenopathies or tumours induces complications at the gastric level. Nausea and vomiting are the most frequent manifestations. However, early epithelial impairments and in particular painful ulcerations, which are often very severe and which may persist after the end of the radiotherapy cycle, may appear.

However, it is the buccal complications of cervicofacial radiotherapy which are the most typical. The initiation of this treatment is marked by a more or less intense mucosal reaction—oropharyngeal mucositis—which is similar to a very severe skin erythema, following a serious burn induced by prolonged exposure to intense ultraviolet radiation of solar origin (very hot summer season or tropical countries). The specificity of the radiomucositis, in particular oropharyngeal radiomucositis, is linked to the specificity of the mucous membrane and to its fragile nature. Unlike the skin integuments which are thick covering tissues, the mucous membranes (buccal, gingival, gastric, intestinal, uterine, vaginal and anorectal) are very fragile because they consist of cellular structures lacking keratin, which are very rich in water and in blood vessels. In such tissues, the molecular agitation induced by high-energy radiation causes an extremely rapid disorganization of the cellular organization which is at the origin of the destruction of the mucous membrane. Unlike the skin tissue, these mucous membranes are not resistant to attacks of this type and do not have any physiological system of protection (e.g.: lipohydrophilic character; rate of renewal, and the like) which is effective against the damage caused by the energy received during each irradiation cycle.

The most deleterious consequences of the oropharyngeal mucositis are the functional discomfort the perception of which can be extremely variable from one patient to another, this discomfort not being linked to the intensity of the clinical symptom. The radiomucositis may therefore be highly crippling, in particular when the erythema is followed by an oedema and then by erosions of the mucous membrane which can, in addition to intense pain, seriously hamper food intake.

In addition, irradiation of the salivary glands, taken in the target volume, causes drying of the mouth, which is often intense and long lasting, or even permanent. In addition to the discomfort of hypoptyalism or of xerostomia (deprivation of saliva), which can also be extremely badly felt, multiple caries may also develop rapidly. At this stage, the major risk of dental lesions, apart from loss of teeth, is requiring the extraction of the tooth on an irradiated bone with the constitution of an osteoradionecrosis, which is essentially mandibular. Thus, the complications of post-irradiation xerostomia are mycoses, repeated bacteria infections, multiple caries and osteoradionecroses and these are frequent, in particular, during radiotherapies of the upper aerodigestive tracts.

Because the mucositis can be aggravated by several cofactors (e.g.: associated chemotherapy [5-FU, cisplatin], nicotine addiction, alcoholism, poor dentibuccal hygiene, and the like) the risks induced by the appearance of radiomucositis may be extremely serious. They therefore justify the search for means for the effective prevention of the erythematous mucosal reaction caused by ionizing radiation.

The authors of the present invention were interested in this question because the current therapeutic means for the prevention or treatment of radiomucositis are not optimized. Indeed, they involve essentially the simultaneous administration of analgesics (e.g.: aspirin), of antifungals (e.g.: amphotericin B, miconazole), of a contact anaesthetic (e.g.: xylocalne) and of mouthwash (based on chlorhexidine and hexamidine) which are systematically repeated.

This is how the idea emerged to develop a composition which is liquid at room temperature, but which is capable of adhering to a mucous membrane because of its passage to the gelled state when the temperatures reaches the temperature of the mucous membrane and which contains substances with anti-free radical activity, while not interfering with the energy emitted by each dose of radiotherapy. Developed to prevent the appearance of buccopharyngeal mucositis following radiotherapy for "head and neck" cancers, this concept of a specifically adapted pharmaceutical preparation can also be applied to other forms of mucositis which are induced by radiotherapy and/or chemotherapy or alternatively combined radiochemo-therapy in the treatment of cancers such as those of the colon, the rectum and the anus or when these therapies incidentally reach the vaginal mucous membrane.

The subject of the present invention is thus a pharmaceutical composition intended in particular for the prevention and the treatment of radiomucositis and of chemomucositis, comprising an effective quantity of a compound having anti-free radical activity in the form of a mixture with a vehicle which is liquid at room temperature and which gels at the temperature of the mucous membrane and which is capable of adhering to the mucous membrane because of its gelled state.

The compound having anti-free radical activity may be in particular chosen from:
1—flavonoids of natural origin, for example:
  i) flavonols or flavonolols, among which:
    a rutoside: rutin (quercitin 3-O-rutino-side), quercitrin (quercetin 3-O-rhamno-side), isoquercitrin (quercetin 3-O-glucoside),
    diosmin (diosmetin 7β-rutinoside), astragalin (kaempferol 3-O-glucoside), kaempferol 3-O-rutinoside, myricitrin (or myricetin 3-O-rhamnoside),
    robinin (or kaempferol 3-O-robinoside 7-rhamnoside),
    kaempferitrin (or kaempferol 3,7-O-dirhamnoside), nobiletin,
    tangeretin.
  ii) flavones, among which:
    rhoifolin (or apigenin 7-O-neohesperido-side), luteolin 7-O-glucoside,
    scutellarin (or scutellarein 5-O-glucoside),
    pectolinarin (or pectolinarigenin 7-O-rutoside),
    galuteolin (or luteolin 5-O-glucoside),
    acaciin (or acacetin 7-O-rhamnoglucoside),
  iii) flavanones, among which:
    liquiritin (or liquiritin 4'-O-glucoside), naringin (or naringenin 7-O-neohesperido-side), hesperidin (or hesperetin 7-O-rut-inoside),
    eriodictin (or eridictiol 7-O-rhamnoside)
2—isoflavonoids of natural origin, for example:
  formononetin 7-O-glucoside (or ononin), afromosin 7-O-glucoside (or wistin),
  genistein (or genistein 7-O-glucoside), daidzin, glycitin,
  genistein 6-O-malonylglucoside, daidzein 6-O-malonylglucoside, genistein 6-O-acetyl-glucoside,
  iridin (or irigenin 7-O-glucoside),
  irisolone,
  tectoridin (or tectorigenin 7-O-glucoside) or shekanin.
3—tocopherols;
4—polyphenols and plant extracts containing polyphenols such as procyanidolic oligomers, extracts of St. John's wort, of *Kallanchoe pinnata*, of camomile, of pine bark, of tea, of *Centella asiatica*, extracts of larch, of edelweiss,
5—vitamins: for example, vitamin A, a carotenoid, alpha-lipoic acid,
6—the active fractions of vegetable oils such as alpha-lupaline, hierogaline,
7—butylated hydroxyanisole, butylated hydroxytoluene.

The vehicle which is liquid at room temperature and which gels at the temperature of the mucous membrane may consist in particular of an aqueous dispersion or solution of a mixture of:
  a—0.05 to 5% by weight (preferably from 0.1 to 3% by weight) of an agent conferring viscosity;
  b—1 to 20% by weight (preferably from 5 to 20% by weight) of an agent modifying the viscosity according to the temperature.

i) The agents conferring viscosity may be chosen in particular from the following compounds:
  colloids or hydrocolloids (polysaccharide substances and related substances):
    galactomannans and derivatives: guar gum, carob gum, tara gum, and the like
    starch and derivatives
    gum arabic, tragacanth gum, karaya gum, and the like
    pectins and derivatives of pectin, and the like
    alginates: alginic acid, sodium alginate, sodium/calcium alginate, and the like
    carrageenans and derivatives, and the like
    cellulose and derivatives: carboxymethyl-cellulose (CMC), sodium carboxymethylcellulose, calcium CMC, methylcellulose, hydroxy-propylcellulose, hydroxypropylmethylcellulose, hydroxyethylcellulose, and the like
    high-molecular weight dextrans
    xanthans and derivatives, and the like
    hyaluronic acid and derivatives, chitin and chitosan and their derivatives, and the like
  polymers of acrylic and methacrylic acids and derivatives: polymethacrylate, carbophilic carboxyvinyl polymer (carbopol, carbomer), polyhydroxyethyl methacrylate,
  polyvinyl derivatives, polyvinylpyrrolidone, poly(vinylpyrrolidone and vinyl acetate), polyvinyl acetatephthalate, polyvinyl alcohol,
  high-molecular weight polyethylene glycols,
  polyacrylamide and derivatives,
  polymers of maleic acid, such as for example: copolymer of polyvinyl ether/maleic acid, sodium/calcium salts of the polyvinyl ether/maleic acid copolymer complex,
  sodium polystyrenesulphonate,
  inorganic derivatives: silica and silicate and silicone derivatives and the like
ii) As examples of agents modifying the viscosity according to the temperature, there may be mentioned:
  poloxamers (e.g.: poloxamer 188, poloxamer 407 and the like) and poloxamines compounds of the divinylbenzenesorbitol type (disorbene), which are soluble in lipophilic medium.

Compositions which have a viscosity of less than $200 \times 10^{-3}$ Pa·s at room temperature (20° C.) and a viscosity greater than $2000 \times 10^{-3}$ Pa·s at 35–37° C. are preferred, the viscosity being determined with an LV type Brookfield viscometer/LV4 rotor/speed of rotation 0.5 rpm/reading after 15 seconds.

By way of example, a solution according to the invention which contains a concentration of agent conferring viscosity—c=1.7% of hydroxymethylpropyl-methylcellulose (HPMC),—with 5% of rutin and 14% of poloxamer 407, exhibits the following behaviour on raising the temperature:

| Temperature (t ° C.) | Viscosity ($10^{-3}$ Pa · s) |
|---|---|
| 25 | 314 |
| 30 | 1433 |
| 35 | 3027 |

Thus, at 25° C. the solution is fluid (viscosity of the order of $300 \times 10^{-3}$ Pa·s) and the gelling is obtained by passage to a temperature of 30° C., then 35° C. (the viscosity is multiplied by 10 between 25 and 35° C.)

The aqueous compositions preferably have pH values which are compatible with the mucous membranes (in general between pH 7 and 8).

The subject of the present invention is also compositions in solid form intended to be mixed with water to form a solution which is liquid at room temperature and which is capable of forming a gel on contact with the mucous membrane to be protected. For the gastric mucous membrane and/or the intestinal mucous membrane, it is thus possible to have solid forms such as a powder or a granule, or alternatively granules which give, upon addition to a liquid vehicle, a liquid composition (example: powder for syrup, for suspension or solution for oral administration to be prepared immediately before use). The compositions may also be provided in the form of bare tablets or granules to be dissolved in water just before use.

The compositions according to the invention may contain other active ingredients combined with the compounds having anti-free radical activity and in particular those belonging to the following pharmacotherapeutic families:

analgesics and antispasmodics (paracetamol, aspirin, codeine, morphine, atropine, loperamide, phloroglucinol, and the like), anaesthetics (xylocalne, lidocaine) and antiseptics (chlorhexidine, hexamidine), anti-inflammatory agents belonging to the corticoid family (prednisolone, triamcinolone, and the like) or oxicams (e.g.: piroxicam, and the like), anti-ulcer agents (antihistamines $H_2$, prostaglandins and derivatives, proton pump inhibitors such as omeprazole, pantoprazole, lanzoprazole), antacids and gastrointestinal dressings (aluminium phosphate, aluminium and magnesium hydroxide, clays (diosmectites, actapulgites, and the like), medicaments for gastrooesophageal reflux and for digestive motivity (sodium alginate, sodium bicarbonate, metoclopramide, and the like), antiemetics (benzamides, antihistamines $H_1$, setrons, and the like), antidiarrhoeals (loperamide, and the like), antifungal with digestive targets (amphotericin B, nystatin, tioconazole, itraconazole, econazole, butoconazole, and the like), medicaments for digestive functional disorders (e.g.: cisapride) and for intestinal transit, intestinal antibacterials (aminoglycosides, nitroimidazoles, polymyxines, and the like) and antivirals (e.g.: acyclovir), products recognized for their soothing and/or cicatrising properties such as: biotin, polyphenols, glycyrrhizinic acid, thymol, eucalyptol, and the like, and extracts of plants rich in glycyrrhetinic acid, pantothenol, allantoin and derivatives, vitamins: of group B (B1, B6, B12), nicotinamide, biotin, pantothenic acid, products correcting hypoptyalism and regulating saliva secretion: pilocarpine, anetholtrithione, peptides and enzymes: elastin, collagen, glutathione, catalase, endonuclease, which can contribute to the repair of tissues lesioned by irradiation.

The following examples illustrate the present invention.

I—Compositions for the Buccal Mucous Membrane

Without being limiting, and to illustrate the invention, the following preparations may be presented as examples:

| | Percentages | | | |
|---|---|---|---|---|
| Examples | 1 | 2 | 3 | 4 |
| Water-soluble rutoside | 2 to 10 | 2 to 10 | 2 to 10 | 2 to 10 |
| Pilocarpine hydrochloride | — | 1 to 5 | — | 1 to 5 |
| Poloxamer 407 | 14.0 | 5 to 20 | 5 to 20 | 5 to 20 |
| HPMC | 1 to 3 | 1 to 3 | 1 to 3 | 1 to 3 |
| Flavouring | 0.1–0.5 | 0.1 to 0.5 | 0.1–0.5 | 0.1 to 0.5 |
| Alpha-tocopherol | — | — | 0.01 to 0.05 | 0.01 to 0.05 |
| Buffer pH 7.8 qs | 100 | 100 | 100 | 100 |

These compositions constitute solutions of thermoreversible consistency: fluid at room temperature (20° –25° C.), viscous at the temperature (35–37° C.) of the physiological cavities. Thus, the viscosity at room temperature (25° C.) of a composition combining 5 to 20% of poloxamer 407 and 1 to 3% of HPMC polymer (that is 6 to 23% of gelling agents) may be sufficiently low (150 to $300 \times 10^{-3}$ Pa·s) to allow easy propulsion (by the delivery system) and then an effective gelling on the mucous membrane to be protected (by passage of the viscosity to $2000$–$21,000 \times 10^{-3}$ Pa·s when the temperature increases between 30 and 35° C., for example).

II—Composition for the Digestive Mucous Membrane

1—Gellable Liquid Composition

As nonlimiting examples, there may be mentioned:

| | Percentages | | | |
|---|---|---|---|---|
| Examples | 5 | 6 | 7 | 8 |
| Rutoside | 2 to 10 | 1 to 5 | 0 to 5 | 0 to 5 |
| Amphoter- | — | 1 to 2.5 | — | — |

-continued

| | Percentages | | | |
|---|---|---|---|---|
| Examples | 5 | 6 | 7 | 8 |
| icine B | | | | |
| Miconazole | — | — | 1 to 5 | — |
| Allantoin | 0 to 1 | 0 to 1 | 0 to 1 | — |
| Biotin | 0 to 0.050 | 0 to 0.050 | 0 to 0.050 | 0 to 0.050 |
| Dexpanthenol | 0 to 1 | 0 to 1 | 0 to 1 | 0 to 1 |
| St John's wort (aqueous extract) | — | — | — | 0 to 5 |
| Kallanchoe (aqueous extract) | — | — | — | 0 to 5 |
| HPMC (Methocel E4M) | 1 to 3 | 1 to 3 | 1 to 3 | 1 to 3 |
| Poloxamer 407 (Lutrol F127) | 6 to 20 | 6 to 20 | 6 to 20 | 6 to 20 |
| Sweetener/flavouring | qs | qs | qs | qs |
| Preservatives | qs | qs | qs | qs |
| Water qs | 100 | 100 | 100 | 100 |

2 Granules to be Dispersed in Water

At the temperature of the gastrointestinal tract, this composition forms a gel adhering to the villosities of the mucous membrane.

| | (mg) | | | |
|---|---|---|---|---|
| Examples | 9 | 10 | 11 | 12 |
| Diosmin | 500 | 500 | 500 | 500 |
| Extract of Centella asiatica | — | 20 to 50 | — | — |
| Hydroxypropyl-methylcellulose (HPMC) | 150 | 150 | 150 | 150 |
| Xanthan gum | 250 | 250 | 250 | 250 |
| Calcium carbonate | 1000 | 1000 | 500 | — |
| Aldioxa* | — | — | 900 | — |
| Alcloxa** | — | — | 100 | — |
| Poloxamer 407 | 1500 | 1500 | 1500 | 1500 |
| Aluminium hydroxide | — | — | — | 400 |
| Magnesium hydroxide | — | — | — | 400 |
| Flavouring | qs | qs | qs | qs |
| Xylitol | 1000 | 1000 | 1000 | 1000 |

*dihydroxyaluminium allantoinate
**chlorhydroxyaluminium allantoinate (for one sachet to be dispersed in a volume of 100 to 200 ml of water)

EXAMPLE 13

Granule to be Dispersed in Water (Preparation for Immediate Use)

At the temperature of the gastrointestinal tract, this composition, in mg for one sachet to be dispersed in 100 ml of water at the time of use, also forms a gel adhering to the villosities of the mucous membrane:

| | |
|---|---|
| OPC* | 200–500 |
| Alpha-lipoic acid | 0–20 |
| Polyvidone | 200 |

-continued

| | |
|---|---|
| β-cyclodextrin | 1000–3000 |
| Hydroxypropylmethylcellulose | 100 |
| Poloxamer 407 | 1000 |
| Flavouring/sweetener | qs |

*procyanidolic oligomers (extract of grape seed and of pine bark)

III—Composition for the Rectal Mucous Membrane

Two examples of ready-to-use thermogellable viscous solutions are given below:

| Examples | 18 (in %) | 19 (in %) |
|---|---|---|
| Rutosides | 2 to 10 | 1 to 5 |
| Dexpanthenol | — | 1 to 5 |
| Butylated hydroxytoluene | — | 1 to 10 |
| Alpha-tocopherol | — | 0.01 to 0.05 |
| (HPMC) Methocel E 4M | 1 to 3 | 1 to 3 |
| Poloxamer 407 | 5 to 20 | 5 to 20 |
| Purified water qs | 100 | 100 |

IV—Compositions for the Vaginal Mucous Membrane

Three nonlimiting examples of solutions which gel at the temperature of the mucous membrane are given below:

| Examples | 20 (in %) | 21 (in %) | 22 (in %) |
|---|---|---|---|
| Rutosides | 0.5 to 10 | 0.5 to 10 | 0.5 to 10 |
| Butoconazole nitrate | 1 to 5 | — | — |
| Econazole nitrate | — | 1 to 3 | — |
| Thioconazole | — | — | 2 to 5 |
| Poloxamer 407 | 6 to 20 | 6 to 20 | 6 to 20 |
| Methocel E 4M | 1 to 2 | 1 to 2 | 1 to 2 |
| Purified water qs | 100 | 100 | 100 |

What is claimed is:

1. A method for treatment of radiomucositis comprising the administration to a mucous membrane of an effective amount of a compound chosen from flavonoids and isoflavonoids in the form of a mixture with a vehicle which is liquid at room temperature and which gels at the temperature of the mucous membrane and which is capable of adhering to the mucous membrane because of its gelled state.

2. The method of claim 1 wherein administration to the mucous membrane occurs prior to radiotherapy or combined radiochemotherapy.

3. A pharmaceutical composition for the treatment of radiomucositis comprising an effective quantity of a compound chosen from flavonoids and isoflavonoids in the form of a mixture with a vehicle which is liquid at room temperature and which gels at the temperature of the mucous membrane and which is capable of adhering to the mucous membrane because of its gelled state.

4. The composition according to claim 3, whose vehicle is an aqueous vehicle and comprises a mixture of 0.05 to 5% by weight of an agent conferring viscosity and of 1 to 20% by weight of an agent modifying the viscosity according to the temperature.

5. The composition according to claim 4, in which the agent modifying the viscosity according to the temperature is chosen from poloxamers, poloxamines, and divinylbenzenesorbitol compounds.

6. The composition according to claim 3, whose vehicle is an aqueous vehicle and comprises a mixture of 0.1 to 3% by weight of an agent conferring viscosity and of 5 to 20% by weight of an agent modifying the viscosity according to the temperature.

7. The composition according to claim 6, in which the agent modifying the viscosity according to the temperature is chosen from poloxamers, poloxamines, and divinylbenzenesorbitol compounds.

8. The composition according to claim 3, in which the flavonoid is chosen from a rutoside, diosmin, quercitin, tangeretin, and hesperidin.

9. The composition according to claim 3, in which the isoflavonoid is genistein, daidzin, or glycitin.

10. The composition according to claim 8, in which the rutoside is rutin.

11. The composition according to claim 3, wherein the vehicle is water.

12. The composition according to claim 3 having a viscosity less than $200 \times 10^{-3}$ Pa·s at 35–37° C.

13. A pharmaceutical composition for the treatment of radiomucositis comprising from 0.5 to 10% of a rutoside in the form of mixture with a vehicle which is liquid at room temperature and which gels at the temperature of the mucous membrane and which is capable of adhering to the mucous membrane because of its gelled state.

14. The composition according to claim 13 containing from 2 to 10% of the rutoside.

15. The composition according to claim 13 containing from 1 to 5% of the rutoside.

16. The composition according to claim 13 whose vehicle is an aqueous vehicle and comprises a mixture of 0.05% to 5% by weight of an agent conferring viscosity and of 1 to 20% by weight of an agent modifying the viscosity according to the temperature.

17. The composition according to claim 15 in which the agent modifying the viscosity according to the temperature is chosen from poloxamers, poloxamines, and divinylbenzenesorbitol compounds.

18. The composition according to claim 13 whose vehicle is an aqueous vehicle and comprises a mixture of 0.1 to 3% by weight of an agent conferring viscosity and of 5 to 20% by weight of an agent modifying the viscosity according to the temperature.

19. The composition according to claim 17 in which the agent modifying the viscosity according to the temperature is chosen from poloxamers, poloxamines, and divinylbenzenesorbitol compounds.

20. The composition according to claim 13 in which the flavanoid is chosen from a rutoside, diosmin, quercitin, tangeretin, and hesperidin.

21. The composition according to claim 13, in which the isoflavonoid is genistein, daidzin, or glycitin.

22. The composition according to claim 13 in which the rutoside is rutin.

23. The composition according to claim 13 wherein the vehicle is water.

24. The composition according to claim 13 having a viscosity less than $22 \times 10^{-3}$ Pa·s at 35–37° C.

* * * * *